United States Patent

Searle et al.

[11] 3,973,035
[45] Aug. 3, 1976

[54] CYANOBENZYL CYCLOPROPANE CARBOXYLATE PESTICIDES

[75] Inventors: Robert J. G. Searle; Roger E. Woodall, both of Sittingbourne; Michael J. Bull, Lower Halstow, all of England

[73] Assignee: Shell Oil Company, Houston, Tex.

[22] Filed: June 23, 1975

[21] Appl. No.: 589,284

Related U.S. Application Data

[62] Division of Ser. No. 469,134, May 13, 1974, Pat. No. 3,914,274.

[30] Foreign Application Priority Data

May 15, 1973 United Kingdom............... 22970/73

[52] U.S. Cl............................. 424/304; 260/465 D
[51] Int. Cl.² ...................... A01N 9/06; A01N 9/20
[58] Field of Search..................... 424/304; 260/465

[56] References Cited
UNITED STATES PATENTS

| 3,835,176 | 9/1974 | Matsuo et al. | 424/304 |
| 3,856,976 | 12/1974 | Hunter et al. | 424/304 |

*Primary Examiner*—V. D. Turner

[57] ABSTRACT

New cyanobenzyl cyclopropane carboxylates of the formula:

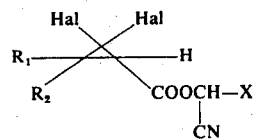

where Hal represents a halogen atom; $R_1$ and $R_2$ each represent an alkyl group; and X represent an optionally substituted phenyl group are useful as pesticides.

5 Claims, No Drawings

CYANOBENZYL CYCLOPROPANE CARBOXYLATE PESTICIDES

This is a division of application Ser. No. 469,134, filed May 13, 1974, now U.S. Pat. No. 3,914,274, issued Oct. 21, 1975.

This invention relates to novel cyanobenzyl cyclopropane carboxylates which are of interest as pesticides, particularly insecticides and acaricides.

Accordingly the present invention provides cyanobenzyl cyclopropane carboxylates having the general formula:

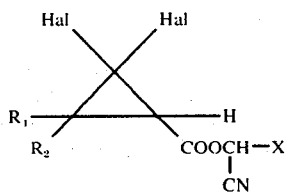

wherein Hal represents a halogen atom; $R_1$ and $R_2$ each represents an alkyl group; and X represents the phenyl group or a phenyl group substituted by one or more non-polar substituents, viz., halogen atoms, or hydrocarbon or hydrocarbonoxy groups having multiple bonds, if any, only interconnecting atoms of carbon. Examples of suitable substituents on the phenyl group thus are halogen, alkyl, alkoxy, alkenyloxy, alkynyloxy, aryloxy, alkaryloxy or aralkyl.

Preferred cyanobenzyl cyclopropane carboxylates are those of formula I wherein Hal represents a chlorine atom; $R_1$ and $R_2$ each represents an alkyl group of 1–6 carbon atoms, especially methyl; and X represents the phenyl group which preferably is substituted by one or more chlorine atoms and/or by one or more alkyl groups of 1–6 carbon atoms, for example, by methyl, and/or by a phenoxy, tolyloxy propargyloxy or benzyl group or other hydrocarbon or hydrocarbonoxy group containing up to about 8 carbon atoms if aliphatic and up to about 14 carbon atoms if aromatic.

Particularly preferred are the aryloxyphenyl and the aralkylphenyl compounds, that is to say, the compounds (Hal being chlorine and $R_1$ and $R_2$ being methyl or other $C_1$–$C_6$ alkyl group(s)) wherein X represents the phenyl group substituted by a single monocyclic aralkyl or monocyclic aryloxy group of from 7 or 6, respectively, up to 15, or 14, respectively carbon atoms, and a preferred species is alpha-cyano-3-phenoxybenzyl 2,2-dichloro-3,3-dimethylclopropane carboxylate.

The cyanobenzyl cyclopropane carboxylates of formula I are prepared by a process which comprises reacting a cyclopropane derivative of formula:

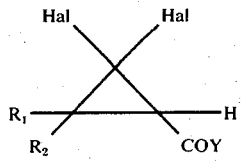

with a compound of formula:

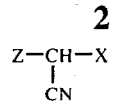

wherein one of the groups Y and Z represents a halogen, suitably chlorine, atom, and the other represents a hydroxy group. The reaction is preferably carried out in the presence of a hydrogen halide acceptor, for example a tertiary amine such as triethylamine, and optionally in an organic solvent, for example an aromatic hydrocarbon solvent, such as toluene.

As mentioned above the cyanobenzyl cyclopropane carboxylates of the invention are of interest as pesticides, particularly as insecticides and acaricides. The compounds also exhibit interesting "knock-down" activity against insect pests such as house flies.

It is well known that various derivatives of cyclopropane carboxylic acid or of certain substituted cyclopropane carboxylic acids are useful as insecticides. These "synthetic pyrethroids", to use the term that is frequently applied to these synthetic products, heretofore have been used mainly as substitutes for, or as equivalents of, the naturally occurring pyrethroid insecticides, and thus have been of interest for their quick knockdown activity, their low persistence as toxic residues, and their low mammalian toxicity. Because of their low persistence, and perhaps also their instability under conditions encountered in open fields where agricultural crops are grown, these synthetic and natural pyrethroids heretofore have been in the main of little if any practical value for protecting agricultural crops from attack by insecticides, for example, cotton, maize, soybeans, etc. A particular advantage of the compounds of the present invention appears to be that they possess a combination of toxicity, stability to light and to atmospheric conditions, and low phytotoxicity which makes the compounds highly useful on commercially valuable agricultural crops. The invention includes therefore pesticidal compositions comprising a cyanobenzyl cyclopropane carboxylate of formula I together with a carrier and/or a surface-active agent. The invention also includes a method of combating insect and/or acarid pests at a locus which comprises applying to the locus a pesticidally effective amount of a cyanobenzyl cylopropane carboxylate or composition of the invention.

The term 'carrier' as used herein means a solid or fluid material, which may be inorganic or organic and of synthetic or natural origin, with which the active compound is mixed or formulated to facilitate its application to the plant, seed, soil or other object to be treated, or its storage, transport or handling. The carrier may be solid or a fluid. Any of the materials usually applied in formulating pesticides may be used as the carrier.

Suitable solid carriers are natural and synthetic clays and silicates, for example natural silicas such as diatomaceous earths; magnesium silicates, for example, talcs; magnesium aluminium silicates, for example, attapulgites and vermiculites; aluminium silicates, for example, kaolinites, montmorillinites and micas; calcium carbonates; calcium sulphate; synthetic hydrated silicon oxides and synthetic calcium or aluminium silicates; elements such as for example, carbon and sulphur; natural and synthetic resins such as, for example coumarone resins, polyvinyl chloride and styrene polymers and copolymers; solid polychlorophenols; bitumen; waxes such as for example, beeswax, paraffin wax, and chlorinated mineral waxes; and solid fertilizers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosine, light mineral oils; chlorinated hydrocarbons, such as for example, carbon tetrachloride, perchloroethylene, trichloroethane, including liquefied normally vaporous gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols, and will generally contain 0.5 to 95% w, preferably 0.5 to 75% w, of toxicant. Wettable powders are usually compounded to contain 25, 50 or 75% w of toxicant and usually contain, in addition to solid carrier, 3–10% w of a dispersing agent and, where necessary, 0–10% w. of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of toxicant. Granules are usually prepared to have a size between 10 and 100 BS mesh (1.676 – 0.152mm), and may be manufactured by agglomeration or impregnation techniques. Generally, granules will contain ½–25% w toxicant and 0–10% w of additives such as stabilizers, slow release modifiers and binding agents. Emulsifiable concentrates usually contain, in addition to the solvent and, when necessary, co-solvent, 10–50% w/v toxicant, 2–20% w/v emulsifiers and 0–20% w/v of appropriate additives such as stabilizers, penetrants and corrosion inhibitors. Suspension concentrates are compounded so as to obtain stable, non-sedimenting, flowable product and usually contain 10–75% w toxicant, 0.5 –15% w of dispersing agents, 0.1–10% w of suspending agents such as protective colloids and thixotropic agents, 0– % w of appropriate additives such as defoamers, corrision inhibitors, stabilizers, penetrants and stickers, and as carrier, water or an organic liquid in which the toxicant is substantially insoluble; certain organic salts may be dissolved in the carrier to assist in preventing sedimentation or as antifreeze agents for water.

The compositions of the invention may contain other ingredients, for example, protective, colloids such as gelatin, glue, casein, gums, cellulose ethers, and polyvinyl alcohol; thixotropic agents e.g. bentonites, sodium polyphosphates; stabilizers such as ethylene diamine tetra-acetic acid, urea, triphenyl phosphate; other compounds having pesticidal, especially insecticidal, acaricidal, herbicidal or fungicidal properties.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The invention is further illustrated in the following examples. It should be understood, however, that the examples given are for the purpose of illustration only, and are not to be regarded as limiting the invention in any way.

EXAMPLE 1 alpha-Cyano-3-phenoxybenzyl 2,2-dichloro-3,3 dimethylcyclopropane carboxylate 2,2-Dichloro-3,3-dimethylcyclopropanoyl chloride (2.69g) was dissolved in dry toluene (50ml) and this solution was added dropwise to a stirred solution of 3-phenoxymandelonitrile (3.0g) and triethylamine (2.69g) in dry toluene (50ml) maintained at 10°C. The mixture was then stirred at room temperature for 16 hours. The mixture was filtered and the filtrate was washed in turn with 5% sulphuric acid, saturated sodium bicarbonate and water, and then dried ($Na_2SO_4$). The solvent was removed under reduced pressure and the residue purified by chromatography on silica gel eluting in turn with toluene, 1 : 1 toluene/hexane and toluene. The required product was obtained as an oil $n_D^{20}$ 1.5630.

Analysis

Calculated for $C_{20}H_{17}NO_3Cl_2$ : C 61.5; H 4.4; N 3.5%
Found : C 61.9; H 4.5; N 3.5%

EXAMPLE 2

Following procedures similar to that described in Example 1 further compounds were prepared, details of which are given in Table 1.

Example 3

Insecticidal and Acaricidal Activity

The insecticidal and acaricidal activity of the compounds of the invention was tested as follows:

1. A 1.0% by weight solution in acetone of the compound to be tested was prepared, and taken up in a micrometer syringe. Two to three-day old adult female house flies (*Musca domestica*) were anaesthetized with carbon dioxide, and 1µl drop of the test solution was brushed off on the ventral abdomen of each, 20 flies being treated. The treated flies were held for 24 hours in glass jars, each containing a little granulated sugar as food for the flies, and the percentage of dead and moribund individuals was then recorded.

II. The compounds were formulated as solutions or suspensions in water containing 20% by weight of acetone and 0.05% by weight of Triton X 100 as wetting agent. The formulations contained 0.7% by weight of the compound to be tested. Turnip and broad bean plants, trimmed to one leaf each, were sprayed on the under surface of the leaf with the above formulation. Spraying was effected with a spraying machine delivering 450 liters per hectare, the plants passing under the spray on a moving belt. Ten adult 1-2 week-old mustard beetles (*Phaedon cochleariae*) were placed on the sprayed leaf of each turnip plant and ten apterous (6-day-old) vetch aphids (*Megoura viciae*) were placed on the sprayed leaf of each broad bean plant. The plants were then enclosed in glass cylinders fitted at one end with a muslin cap. Mortality counts were made after 24 hours.

III. In tests against glass house spider mites (*Tetranychus urticae*) leaf discs cut from French bean plants were sprayed in the manner described under II. 1 hour after spraying, the discs were inoculated with 10 adult mites. Mortality counts were made 24 hours after inoculation.

IV. In tests against large white butterfly larvae (*Pieris brassicae*), leaf discs cut from cabbage leaves were sprayed in the manner described under II. 10 3rd instar (8–10 day-old) larvae were placed on the discs within petri-dish pairs. Mortality counts were again made 24 hours after inoculation.

The results of these tests are shown in Table 2, in which A denotes complete kill, B some kill and C no kill of the test species.

Example 4
"Knock-down" activity against houseflies

About 70 houseflies (*Musca domestica*) were introduced into a transparent glass cylinder (61 cm × 30 cm diam) through a sliding panel at one end. 0.2 ml of a solution of the test compound in a mixture containing 20% methylene dichloride in Shellsol K was sprayed into the chamber over a period of 1–5 seconds at a pressure of 10 psi. The air supply was maintained for a further 2 seconds to aid the uniform distribution of the spray. Knock-down counts were made at intervals during the 10 minute period immediately after spraying.

In this test the compound: α-cyano-3-phenoxybenzyl 2,2-dichloro-3,3-dimethylcylcopropane carboxylate gave a knock-down of 90% or more after 8.5 minutes using a concentration of the compound in the test solution of 0.1% w/v.

Table 1

| Compound | Refractive Index | Analysis | |
|---|---|---|---|
| alpha-cyano-2,6-dichlorobenzyl 2,2-dichloro-3,3-dimethyl cyclopropane carboxylate | $n_D^{20}$ 1.5550 | Calculated for $C_{14}H_{11}Cl_4NO_2$ Found | C 45.8; H 3.0; N 3.8% C 46.0; H 3.1; N 3.7% |
| alpha-cyano-2,4,6-trimethyl-benzyl 2,2-dichloro-3,3-dimethyl cyclopropane carboxylate | $n_D^{20}$ 1.5331 | Calculated for $C_{17}H_{19}Cl_2NO_2$ Found | C 60.0; H 5.6; N 4.1% C 60.0; H 5.7; N 4.1% |
| alpha-cyano-3-tolyloxybenzyl 2,2-dichloro-3,3-dimethyl cyclopropane carboxylate | $n_D^{20}$ 1.5580 | Calculated for $C_{21}H_{23}Cl_2NO_3$ Found | C 61.8; H 5.6; N 3.4% C 61.7; H 5.4; N 3.1% |
| alpha-cyano-3-propargyloxybenzyl 2,2-dichloro-3,3-dimethyl cyclopropane carboxylate | $n_D^{20}$ 1.5386 | Calculated for $C_{17}H_{15}Cl_2NO_3$ Found | C 57.9; H 4.3; N 4.0% C 58.3; H 4.3; N 3.8% |
| alpha-cyanobenzyl 2,2-dichloro-3,3-dimethyl cyclopropane carboxylate | $n_D^{20}$ 1.5310 | Calculated for $C_{14}H_{13}Cl_2NO_2$ Found | C 56.4; H 4.4; N 4.7% C 56.8; H 4.6; N 4.6% |
| alpha-cyano-3-benzylbenzyl 2,2-dichloro-3,3-dimethyl cyclopropane carboxylate | $n_D^{20}$ 1.5641 | Calculated for $C_{21}H_{19}Cl_2NO_2$ Found | C 65.0; H 4.9; N 3.6% C 65.3; H 5.2; N 3.6% |

Table 2

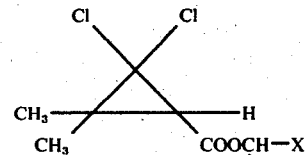

| | | | Pesticidal Activity | | |
|---|---|---|---|---|---|
| Compound X | M. domestica | P. cochleariae | P. brassicae | M. viciae | T. urticae |
| 3-p-tolyloxyphenyl | A | A | A | A | A |
| 3-p-tolylphenyl | A | A | A | A | A |

We claim:
1. A method of combating insect or acarid pests at a locus which comprises applying to the locus a pesticidally effective amount of a cyanobenzyl cyclopropane carboxylate of the formula

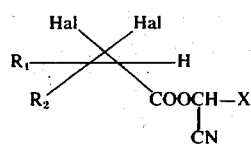

wherein Hal represents a chlorine atom; $R_1$ and $R_2$ each represents an alkyl group of 1 to 6 carbon atoms; and X represents a phenyl group optionally substituted by one or more chlorine atoms, by one or more alkyl groups of 1 to 6 carbon atoms or by a phenoxy, tolyloxy, propargyloxy or benzyl group, or a composition of said carboxylate with at least one carrier or surface-active agent.

2. A method as claimed in claim 1 wherein $R_1$ and $R_2$ each represents a methyl group and X represents a phenyl group optionally substituted by one or more chlorine atoms or methyl groups or by a phenoxy, tolyloxy, propargyloxy or benzyl group.

3. A method as claimed in claim 2 wherein the cyanobenzyl cyclopropane carboxylate is alpha-cyano-3-phenoxybenzyl 2,2-dichloro-3,3-dimethyl cyclopropane carboxylate.

4. A method as claimed in claim 2 wherein the cyanobenzyl cyclopropane carboxylate is alpha-cyano-3-tolyloxybenzyl 2,2-dichloro-3,3-dimethyl cyclopropane carboxylate.

5. An insecticidal or acaricidal composition comprising an insecticidally or acaricidally effective amount of a cyanobenzyl cyclopropane carboxylate as shown in claim 1 together with at least one carrier or surface-active agent.

* * * * *